US012570942B2

(12) United States Patent
Kuninori et al.

(10) Patent No.: US 12,570,942 B2
(45) Date of Patent: Mar. 10, 2026

---

(54) BIOLOGICAL TISSUE FORMING DEVICE AND METHOD FOR FORMING BIOLOGICAL TISSUE

(71) Applicant: TOYO SEIKAN GROUP HOLDINGS, LTD., Tokyo (JP)

(72) Inventors: Masahiro Kuninori, Kanagawa (JP); Kazuhiro Tsuruta, Kanagawa (JP); Kentarou Ichikawa, Kanagawa (JP)

(73) Assignee: TOYO SEIKAN GROUP HOLDINGS, LTD., Tokyo (JP)

( * ) Notice: Subject to any disclaimer, the term of this patent is extended or adjusted under 35 U.S.C. 154(b) by 586 days.

(21) Appl. No.: 18/083,569

(22) Filed: Dec. 19, 2022

(65) Prior Publication Data

US 2023/0118544 A1 Apr. 20, 2023

Related U.S. Application Data

(63) Continuation of application No. PCT/JP2021/023656, filed on Jun. 22, 2021.

(30) Foreign Application Priority Data

Jun. 25, 2020 (JP) ................................. 2020-109308

(51) Int. Cl.
| | |
|---|---|
| *C12M 1/12* | (2006.01) |
| *C12M 1/42* | (2006.01) |
| *C12N 5/00* | (2006.01) |

(52) U.S. Cl.
CPC ............ *C12M 25/04* (2013.01); *C12M 25/14* (2013.01); *C12M 35/08* (2013.01); *C12N 5/0068* (2013.01); *C12N 2533/30* (2013.01)

(58) Field of Classification Search
CPC ...... C12M 25/04; C12M 25/14; C12M 25/02; C12M 35/08; C12M 21/08; C12M 23/16; C12N 5/0068; C12N 2533/30
See application file for complete search history.

(56) References Cited

U.S. PATENT DOCUMENTS

| | | |
|---|---|---|
| 2011/0003359 A1 | 1/2011 | Fujiyama et al. |
| 2016/0313306 A1 | 10/2016 | Ingber et al. |
| | (Continued) | |

FOREIGN PATENT DOCUMENTS

| | | |
|---|---|---|
| JP | 2017-504320 A | 2/2017 |
| WO | 2009/099066 A1 | 8/2009 |
| | (Continued) | |

OTHER PUBLICATIONS

Office Action issued in Chinese Patent Application No. 202180036598.8 dated Dec. 14, 2024, with English Translation (19 pages).

(Continued)

*Primary Examiner* — Michael L Hobbs
(74) *Attorney, Agent, or Firm* — Nakanishi IP Associates, LLC

(57) ABSTRACT

A biological tissue forming device that ensures a cell-cell interaction and an exchange of liquid components between cell layers of a formed biological tissues with high efficiency can be provided. A biological tissue forming device for forming a biological tissue having a plurality of cell layers formed of adherent cells has both surfaces on which culture regions of the adherent cells are disposed, and includes a culture membrane arranged between the plurality of cell layers after the adherent cells are cultured and a plurality of flow passages divided by the culture membrane. The culture membrane is formed of a readily-soluble material.

6 Claims, 6 Drawing Sheets

(56)                    References Cited

U.S. PATENT DOCUMENTS

| | | | |
|---|---|---|---|
| 2018/0216058 A1 | 8/2018 | Huh et al. | |
| 2018/0223251 A1 | 8/2018 | Huh et al. | |
| 2018/0230415 A1* | 8/2018 | Huh | A61L 27/3633 |
| 2018/0356399 A1* | 12/2018 | Ito | G01N 33/5088 |
| 2021/0003561 A1 | 1/2021 | Ingber et al. | |
| 2021/0348095 A1 | 11/2021 | Huh et al. | |
| 2023/0151316 A1 | 5/2023 | Huh et al. | |
| 2024/0218306 A1 | 7/2024 | Huh et al. | |
| 2024/0248077 A1 | 7/2024 | Ingber et al. | |
| 2024/0368507 A1 | 11/2024 | Huh et al. | |

FOREIGN PATENT DOCUMENTS

| | | |
|---|---|---|
| WO | 2011/118582 A1 | 9/2011 |
| WO | 2015/138034 A2 | 9/2015 |
| WO | 2018/226902 A2 | 12/2018 |

OTHER PUBLICATIONS

International Search Report issued in PCT/JP2021/023656 mailed on Sep. 14, 2021 with English Translation (6 pages).

Written Opinion of the International Searching Authority issued in PCT/JP2021/023656 mailed on Sep. 14, 2021 with English Translation (8 pages).

Office Action issued in Japanese Patent Application No. 2022-532501 mailed on Jul. 8, 2025, with English Translation (13 pages).

Extended European Search Report issued in European Patent Application No. 21828931.2, dated Apr. 4, 2025 (8 pages).

Notice of Decision of Refusal issued for Japanese Patent Application No. 2022-532501, mailed on Dec. 2, 2025, with English Translation (12 pages).

* cited by examiner

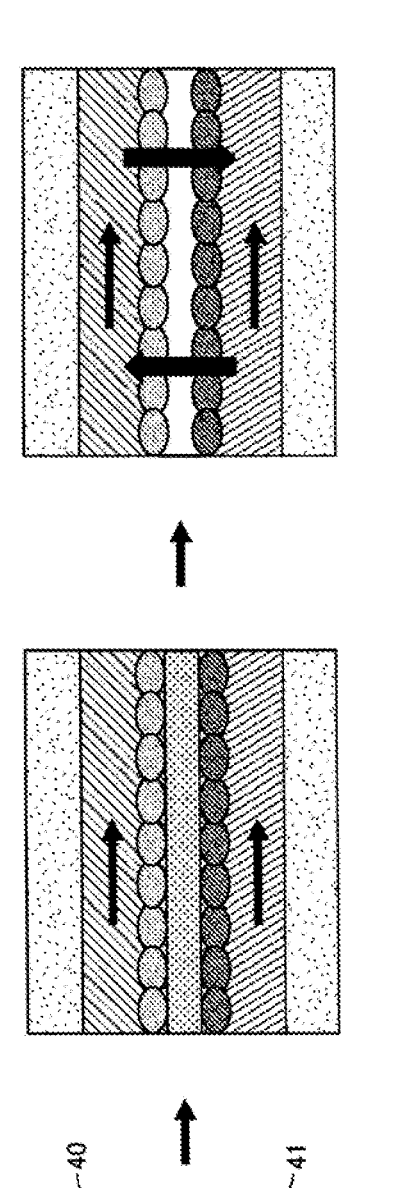
Fig. 4
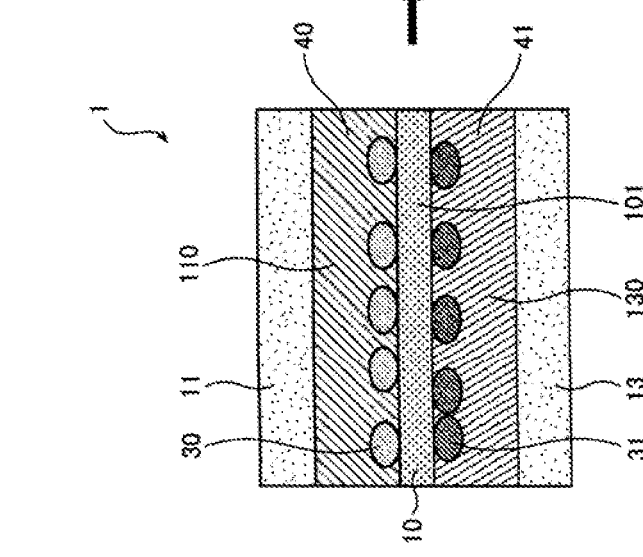

BIOLOGICAL TISSUE FORMING DEVICE AND METHOD FOR FORMING BIOLOGICAL TISSUE

TECHNICAL FIELD

The present invention relates to a cell culture technique, in particular, relates to a device for forming a biological tissue and a method for forming a biological tissue by culturing cells.

BACKGROUND ART

Conventionally, there has been a problem in, for example, developing pharmaceutical medicines, that, regarding a drug candidate substance, when a human pharmacokinetics is unpredictable by a preclinical test and its toxicity is proven in a clinical test, thereby cancelling the development, research and development expenses until then becomes wasteful.

That is, in the preclinical test, a cell-based assay, animal testing, and the like are carried out, but there has been a problem that a pharmacokinetics is unevaluable because the cell-based assay cannot reproduce an in-vivo bloodstream and the like, and a development of cell-specific function is insufficient.

In the animal testing, a result of the pharmacokinetics does not necessarily correspond with that of the human because of the species difference, and therefore, there has been a problem that the pharmacokinetics of the human is hard to predict.

In such conditions, recently, an organ-on-a-chip is expected to solve these various problems as a device configured to improve a prediction accuracy of the pharmacokinetics in the human.

The organ-on-a-chip is a reproduction of an organ tissue structure in a microfluidic device, and for the organ-on-a-chip, there have already been proposed a lung-on-a-chip that models a lung structure, one that models a structure of an enterohepatic circulation by combining a small bowel model and a liver model, one that models a kidney structure, such as a glomerulus model and a proximal convoluted tubule model, and the like.

Here, in an in vitro culture system, which uses a conventional culture dish or the like, a culture environment is semi-static and a supply of oxygen and nutrition and a removal of wastes only depend on a diffusion without reproducing a bloodstream, and therefore, it has been difficult to carry out a test that takes specific functions of cells and interactions between organs into account.

In contrast to this, the organ-on-a-chip ensures reproducing a bloodstream by a pump liquid delivery, and thus, the supply of oxygen and nutrition and the like can be changed by a flow rate, and therefore, it is possible to preferably carry out the test that includes the specific functions of cells and the interactions between organs.

CITATION LIST

Patent Literature

Patent Document 1: JP-T-2017-504320

DISCLOSURE OF THE INVENTION

Problems to be Solved by the Invention

One of such organ-on-a-chips includes flow passages divided into two by a membrane having both surfaces on which cells are cultured to form two cell layers with the membrane interposed therebetween. A semipermeable membrane is used for the membrane, and liquid components, such as nutrients and salts, are exchanged between the two cell layers via holes on the semipermeable membrane.

There are, however, a problem that an interaction between the cell layers is reduced because the semipermeable membrane has hole diameters through which a cell does not pass, and therefore, it interferes with the cells between the cell layers from contacting one another, and a problem that an exchange efficiency of the liquid components is reduced because the holes are easily blocked as the cell layers are formed by the cell culture.

Then, as a result of extensive studies, the present inventors have developed an organ-on-a-chip (a biological tissue forming device) that ensures a cell-cell interaction and an exchange of liquid components between cell layers of a formed biological tissue with high efficiency.

Specifically, first, a readily-soluble material is used for a membrane of the organ-on-a-chip, and the membrane is dissolved after the cell layers are formed on both surfaces of this membrane, thereby making it possible to prevent reductions in cell-cell interaction and exchange efficiency of liquid components between the two cell layers.

Incidentally, while the membrane formed of the readily-soluble material serves a function as a scaffold material for the cells in forming the cell layers on both the surfaces, this scaffold does not exist any longer after the dissolution of the readily-soluble material, and therefore, the formed cell layers are easily broken in some cases.

Therefore, the present inventors further made it possible for the cell layers to be irrefrangible even after the dissolution of the readily-soluble material by forming the membrane with the readily-soluble material and a poorly-soluble material and causing the poorly-soluble material to serve as a support body of the cell layers after the dissolution of the readily-soluble material.

Here, Patent Document 1 discloses a lung-on-a-chip and describes that a biocompatible polymer can be used as a membrane in this lung-on-a-chip (Claim 53 in the Patent Document 1). Patent Document 1 also describes that "biocompatible" refers to any material that does not deteriorate appreciably and does not induce a significant immune response or deleterious tissue reaction (e.g., toxic reaction or significant irritation) over time when implanted into or placed adjacent to the biological tissue of a subject, or induce blood clotting or coagulation when it comes in contact with blood (paragraph 0055), and both biocompatible and biodegradable materials can be used in the present device to facilitate in vivo implantation of the present device (paragraph 0316).

For this lung-on-a-chip, however, a configuration of dissolving the membrane is neither described nor suggested. There is again no configuration disclosed to make the cell layers irrefrangible after the dissolution of the membrane.

The present invention was made in view of the above circumstances. An object of the present invention is to provide a biological tissue forming device and a method for forming a biological tissue that ensures a cell-cell interaction and an exchange of liquid components between cell layers of a formed biological tissue with high efficiency and is capable of making the cell layers irrefrangible.

Solutions to the Problems

In order to achieve the above-described objects, the biological tissue forming device of the present invention is a biological tissue forming device for forming a biological tissue having a plurality of cell layers formed of adherent cells that has a configuration including a culture membrane having both surfaces on which culture regions of the adherent cells are disposed, the culture membrane being arranged between the plurality of cell layers after the adherent cells are cultured, and a plurality of flow passages divided by the culture membrane. The culture membrane is formed of a readily-soluble material.

Another configuration of the biological tissue forming device of the present invention is a biological tissue forming device for forming a biological tissue having a plurality of cell layers formed of adherent cells that has a configuration including a culture membrane having both surfaces on which culture regions of the adherent cells are disposed, the culture membrane being arranged between the plurality of cell layers after the adherent cells are cultured, and a plurality of flow passages divided by the culture membrane. The culture membrane is formed of a readily-soluble material and a poorly-soluble material.

The biological tissue forming device of the present invention is also preferred to have a configuration in which the readily-soluble material in the culture membrane is dissolved to form holes that pass through the culture membrane.

The biological tissue forming device of the present invention is also preferred to have a configuration in which a porous membrane formed of the poorly-soluble material has hole diameters of 10 microns or more in diameter.

Furthermore, the biological tissue forming device of the present invention is also preferred to have a configuration in which the readily-soluble material and the poorly-soluble material serve as a scaffold in culturing the adherent cells.

The biological tissue forming device of the present invention is also preferred to have a configuration in which the poorly-soluble material serves as a support body for the cell layers after the dissolution of the readily-soluble material in the culture membrane.

Furthermore, the biological tissue forming device of the present invention is also preferred to have a configuration in which the poorly-soluble material is formed of any one of polyethylene terephthalate, polylactic acid, or an ultraviolet ray curable resin.

The biological tissue forming device of the present invention is also preferred to have a configuration in which the culture membrane is a porous membrane.

The biological tissue forming device of the present invention is also preferred to have a configuration including the one culture membrane, and two flow passages divided by the culture membrane. A biological tissue having two cell layers is formed.

Furthermore, the biological tissue forming device of the present invention is also preferred to have a configuration in which the two flow passages are formed with respective surfaces on flow passage sides of two plates having flow passages adhered on both respective surfaces of the culture membrane.

The biological tissue forming device of the present invention is also preferred to have a configuration in which in the two flow passages, cell layers formed of adherent cells of respective different kinds are formed.

Furthermore, the biological tissue forming device of the present invention is also preferred to have a configuration in which the readily-soluble material is formed of a water-soluble polymer.

The biological tissue forming device of the present invention is also preferred to have a configuration in which the water-soluble polymer is polyvinyl alcohol, alginic acid, or methyl cellulose.

The method for forming a biological tissue of the present invention is a method for forming a biological tissue having a plurality of cell layers formed of adherent cells, the method includes a step of supplying the adherent cells and a culture fluid to two flow passages in a biological tissue forming device, the biological tissue forming device having both surfaces on which culture regions of the adherent cells are disposed, the biological tissue forming device including a culture membrane arranged between the plurality of cell layers after the adherent cells are cultured and the two flow passages divided by the culture membrane, the culture membrane being formed of a readily-soluble material, a step of culturing the adherent cells in the two flow passages to form the cell layers on both the surfaces of the culture membrane, and a step of dissolving the culture membrane.

Another configuration of the method for forming a biological tissue of the present invention is a method for forming a biological tissue having a plurality of cell layers formed of adherent cells, the method includes a step of supplying the adherent cells and a culture fluid to two flow passages in a biological tissue forming device, the biological tissue forming device having both surfaces on which culture regions of the adherent cells are disposed, the biological tissue forming device including a culture membrane arranged between the plurality of cell layers after the adherent cells are cultured and the two flow passages divided by the culture membrane, the culture membrane being formed of a readily-soluble material and a poorly-soluble material, a step of culturing the adherent cells in the two flow passages to form the cell layers on both the surfaces of the culture membrane, and a step of dissolving the readily-soluble material in the culture membrane.

The method for forming a biological tissue of the present invention is also preferred to be a method in which the readily-soluble material is alginic acid, an alginic acid degrading enzyme is supplied to at least any one of the two flow passages in the step of dissolving, and the readily-soluble material in the culture membrane is dissolved.

Furthermore, the method for forming a biological tissue of the present invention is also preferred to be a method in which the readily-soluble material is polyvinyl alcohol, the biological tissue forming device is heated in the step of dissolving, and the readily-soluble material in the culture membrane is dissolved.

The method for forming a biological tissue of the present invention is also preferred to be a method in which the readily-soluble material is methyl cellulose, the biological tissue forming device is cooled in the step of dissolving, and the readily-soluble material in the culture membrane is dissolved.

Effects of the Invention

According to the present invention, it is possible to provide a biological tissue forming device and a method for forming a biological tissue that ensures a cell-cell interaction and an exchange of liquid components between cell layers of a formed biological tissue with high efficiency and is capable of making the cell layers irrefrangible.

BRIEF DESCRIPTION OF DRAWINGS

FIG. 4 is a schematic diagram illustrating a formation process of cell layers by a biological tissue forming device according to a first embodiment of the present invention.

DESCRIPTION OF EMBODIMENTS

Hereinafter, embodiments of the biological tissue forming device and the method for forming a biological tissue according to the present invention will be described in detail. Note that the present invention is not limited to the specific contents of the following embodiments.

First Embodiment

First, a biological tissue forming device according to a first embodiment of the present invention will be described.

The biological tissue forming device of the embodiment is a device for forming a biological tissue having a plurality of cell layers formed of adherent cells, and can be configured as, what is called, an organ-on-a-chip and the like.

The organ-on-a-chip uses a microfluidic device to reproduce an organ tissue structure in the device, and can precisely control a culture environment of the cells. Therefore, it has an advantage that the cells develop cell functions similar to those developed in vivo.

The biological tissue forming device of the embodiment has both surfaces on which culture regions of the adherent cells are disposed, and includes a culture membrane arranged between the plurality of cell layers after the adherent cells are cultured and a plurality of flow passages divided by the culture membrane. The culture membrane is formed of a readily-soluble material.

Figure 1:
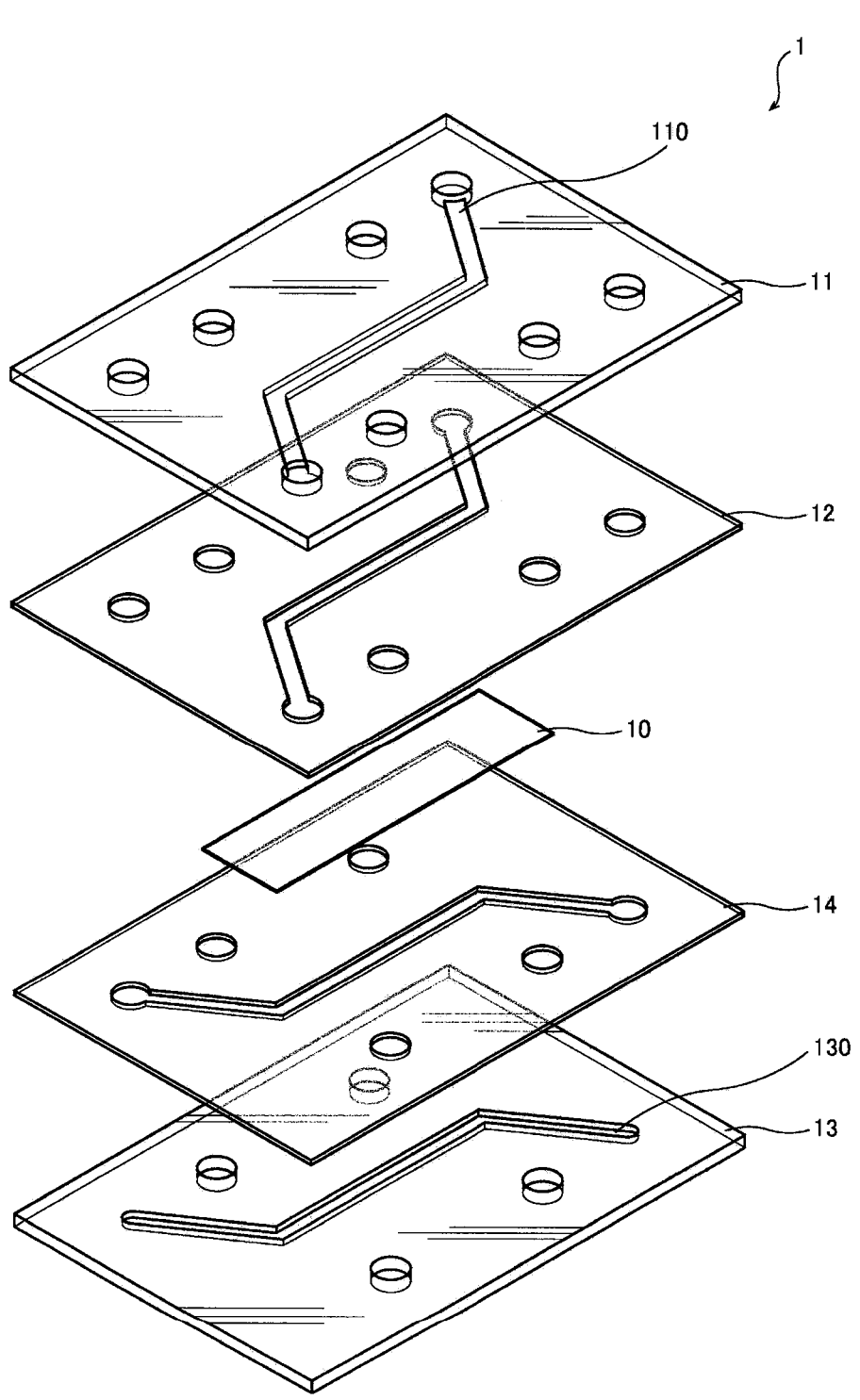
FIG. 1 is a schematic diagram illustrating constituting members of a biological tissue forming device according to respective embodiments of the present invention.
Figure 2:
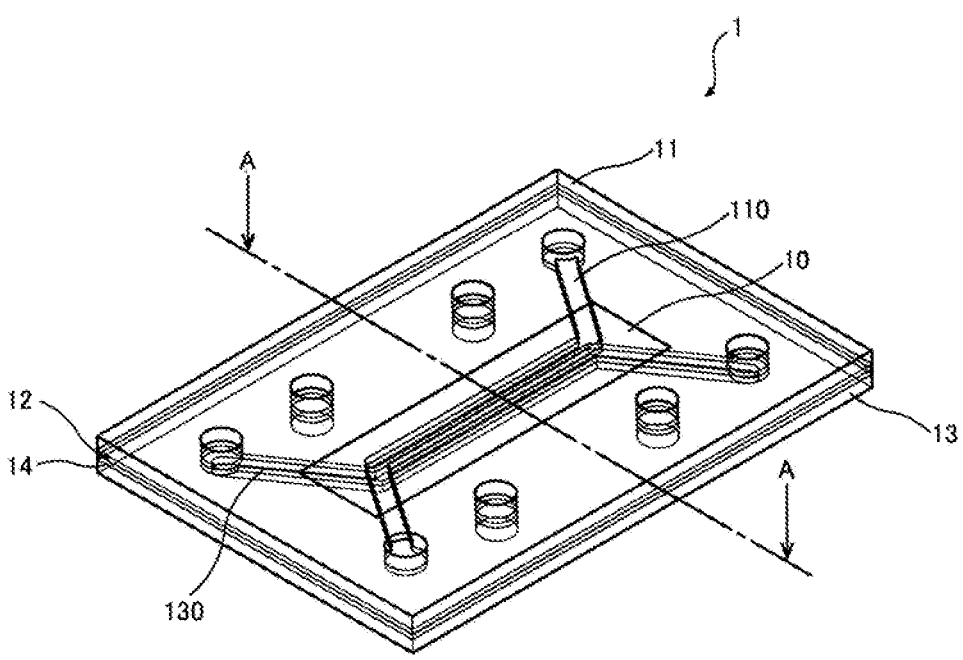
FIG. 2 is a schematic diagram illustrating a configuration of the biological tissue forming device according to the respective embodiments of the present invention.
Figure 3:
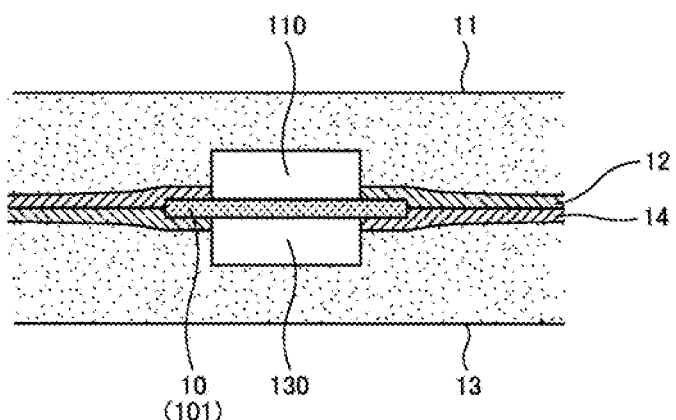
FIG. 3 is a schematic diagram illustrating an A-A cross-sectional surface of the biological tissue forming device according to the respective embodiments of the present invention.

For example, as illustrated in FIGS. 1 to 3, a biological tissue forming device 1 of the embodiment can be manufactured by arranging a culture membrane 10 having surfaces for culturing the adherent cells between a flow passage plate 11 and a flow passage plate 13, and adhering them with adhesive layers 12 and 14 to be integrated. Note that it is also possible for the biological tissue forming device 1 to have a configuration that can form three or more layers of the cell layers by further including a culture membrane and an adhesive layer.

The flow passage plate 11 includes a flow passage 110 and the flow passage plate 13 includes a flow passage 130, and respective surfaces on flow passage sides of these two plates are adhered on both the surfaces of the culture membrane 10 via the respective adhesive layers, and thus, the two flow passages divided by the culture membrane 10 are formed in the biological tissue forming device 1. These flow passages are used as culture chambers.

In these flow passages, respective cell layers are formed on both the surfaces of the culture membrane 10, thereby forming a biological tissue with two cell layers in the biological tissue forming device 1.

These two cell layers may be formed of adherent cells of the same kind or may be formed of adherent cells of respective different kinds, and in particular, it is beneficial that they are formed of adherent cells of different kinds.

In the biological tissue forming device 1 of the embodiment, the culture membrane 10 is formed of a readily-soluble material 101. While this culture membrane 10 may be a porous membrane or may be a non-porous membrane, it is preferred to be a porous membrane having hole diameters of an extent that the cells do not pass through until the readily-soluble material 101 is dissolved. These hole diameters are preferably 0.4 microns to 8 microns in diameter, and is more preferably a diameter of 3 microns to 6 microns.

For the readily-soluble material 101, for example, a water-soluble polymer is usable, and, for example, polyvinyl alcohol (PVA), alginic acid, and methyl cellulose are preferably usable.

When the alginic acid is used as the readily-soluble material 101, feeding an alginic acid degrading enzyme into the flow passage 110 or the flow passage 130 ensures dissolving the culture membrane 10 in the biological tissue forming device 1.

When the polyvinyl alcohol is used as the readily-soluble material 101, heating the biological tissue forming device 1 to, for example, 37° C. to 50° C. after forming the cell layers ensures dissolving the readily-soluble material 101 in the culture membrane 10 in the biological tissue forming device 1. Note that a dissolution temperature of the polyvinyl alcohol is not limited to this range, and it is also possible to dissolve the polyvinyl alcohol by heating to 37° C. to 80° C.

Furthermore, when the methyl cellulose is used as the readily-soluble material 101, cooling the biological tissue forming device 1 to, for example, 5° C. to 10° C. after forming the cell layers ensures dissolving the readily-soluble material 101 in the culture membrane 10 in the biological tissue forming device 1. Note that a dissolution temperature of the methyl cellulose is not limited to this range, and it is also possible to dissolve the methyl cellulose by cooling to 4° C. to 25° C.

Here, the methyl cellulose is a material that is gelatinized at a high temperature and liquefies when cooled, and can be dissolved to bring it into a low-temperature state. In order to adjust the dissolution temperature of the methyl cellulose, it is also preferred to add an additive. Adding the additive into the methyl cellulose ensures increasing its dissolution temperature. For this additive, for example, styrenesulfonic acid sodium (NaSS) is preferably usable.

Thus, with the biological tissue forming device 1 of the embodiment, dissolving the culture membrane 10 after forming the cell layers ensures preferably transmitting liquid components between the plurality of cell layers.

For the cells cultured using the biological tissue forming device 1 of the embodiment, for example, pluripotent stem cells (for example, iPS cells) and embryonic stem cells (ES cells) are usable.

In the biological tissue forming device 1 of the embodiment, it is also preferred to provide a scaffold material for the cells in order to preferably adhere the cells on the surfaces of the culture membrane. The same applies to a second embodiment described later.

Specifically, it is preferred to adhere and culture the cells after adding the scaffold material of the cells on the surfaces of the culture membrane.

For the scaffold material of the cells, for example, collagen, Matrigel, fibronectin, laminins, and chitosan are preferably usable, and it is also possible to use two or more of these materials.

Examples of the method for adding the cellular scaffold material on the surfaces of the culture membrane can include, for example, a method of coating the surfaces of the culture membrane, a method of mixing the readily-soluble material and the cellular scaffold material, a method of chemically bonding the cellular scaffold material to the readily-soluble material using a reagent, such as a coupling agent, and a method of laminating a product preliminarily processed collagen or chitosan into a fiber form on the surfaces of the culture membrane.

It is also preferred to adhere the cells on the surfaces of the culture membrane by adhering the cells on a poorly-soluble material used in the second embodiment described later.

The culture membrane 10 in the biological tissue forming device 1 of the embodiment is, for example, manufactured by applying the readily-soluble material 101 over a base material, stripping the obtained culture membrane 10 off of the base material, and cutting it into a desired shape, and can be used by disposing it in the biological tissue forming device 1.

Note that it is needless to say that the shape of the culture membrane 10 is not limited to the shape illustrated in FIG. 1, and, for example, is also possible to have a shape for arrangement on entire lower surfaces of the flow passage plates 11 and 13.

It is also preferred to perform a surface treatment, such as a corona treatment, an excimer treatment, or a plasma treatment on the surfaces of the culture membrane 10.

Performing such a surface treatment ensures an improvement in hydrophilicity of the surfaces of the culture membrane 10, thereby ensuring an improvement in adhesiveness of the adherent cells onto the surfaces of the culture membrane 10.

For the material of the flow passage plate 11 and the flow passage plate 13 in the biological tissue forming device 1 of the embodiment, for example, cycloolefin polymer, polymethyl methacrylate, and polycarbonate are usable, and the flow passage plate 11 and the flow passage plate 13 can be manufactured by, for example, injection molding.

For the material of the adhesive layer 12 and the adhesive layer 14 in the biological tissue forming device 1 of the embodiment, for example, an adhesive agent is usable, and the adhesive layer 12 and the adhesive layer 14 can be manufactured by, for example, punching into the shape as illustrated in FIG. 1.

Furthermore, for the material of the culture membrane 10 in the biological tissue forming device 1 of the embodiment, as described above, alginic acid, polyvinyl alcohol, and the like can be used, and the obtained culture membrane 10 can be cut into a desired shape and used.

The flow passage plates 11, 13 and the culture membrane 10 are then attached together with the adhesive layers 12, 14 to ensure manufacturing the biological tissue forming device 1 of the embodiment.

The biological tissue forming device 1 of the embodiment may be in a state before the cell layers are formed on the culture membrane 10 or may be in a state after the cell layers are formed on the culture membrane 10.

The biological tissue forming device 1 of the embodiment includes one that has the readily-soluble material 101 dissolved after the cell layers are formed on the culture membrane 10.

Furthermore, it is also preferred that the biological tissue forming device 1 of the embodiment is formed with the culture membrane 10 including the adherent cells. In such a case, the configuration may have the adherent cells fixed on the surfaces of the culture membrane 10 or the configuration may have the adherent cells contained in the culture membrane 10. The adherent cells can be alive in the culture membrane 10 when the culture membrane 10 is manufactured by, for example, the alginic acid.

The biological tissue forming device 1 of the embodiment with such a configuration ensures omitting a supply of the adherent cells to the flow passages in the method for forming a biological tissue of the embodiment described later.

The method for forming a biological tissue of the embodiment is a method for forming a biological tissue having a plurality of cell layers formed of adherent cells, and includes a step of supplying the adherent cells and a culture fluid to two flow passages in a biological tissue forming device having both surfaces on which culture regions of the adherent cells are disposed, including a culture membrane arranged between the plurality of cell layers after the adherent cells are cultured and the two flow passages divided by the culture membrane, and the culture membrane being formed of a readily-soluble material, a step of culturing the adherent cells in the two flow passages to form the cell layers on both the surfaces of the culture membrane, and a step of dissolving the culture membrane.

Figure 7:
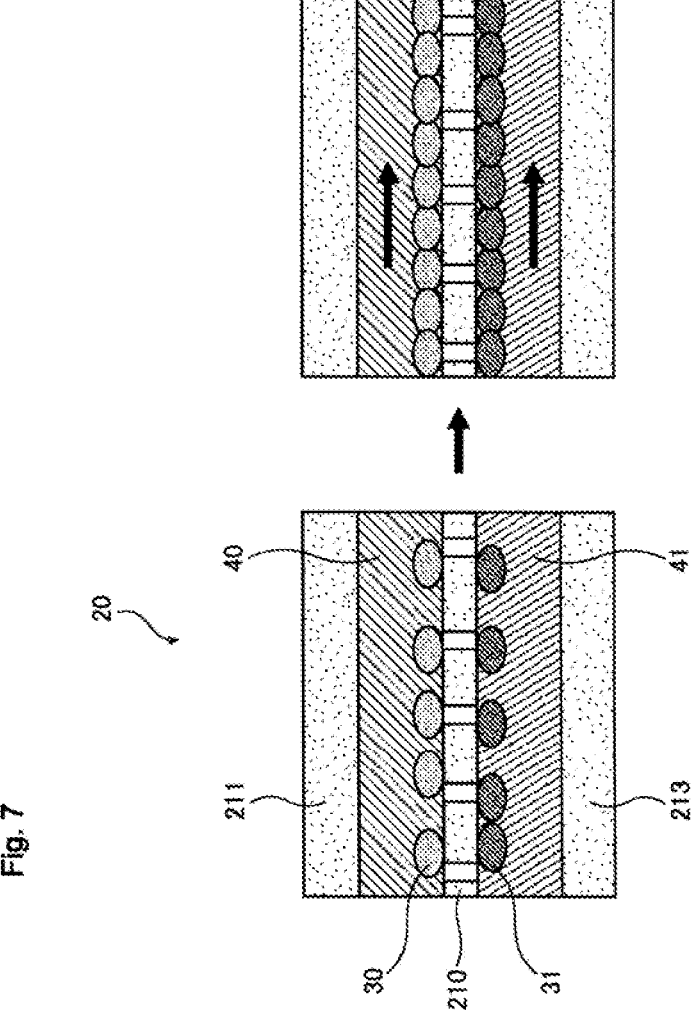
FIG. 7 is a schematic diagram illustrating a formation process of cell layers by a conventional biological tissue forming device.

Here, as illustrated in FIG. 7, for a conventional biological tissue forming device 20, a semipermeable membrane, such as polyester, is typically used as a culture membrane 210, and a cell-cell interaction and an exchange of liquid components take place between two flow passages via this membrane.

That is, in the conventional biological tissue forming device 20, the two cell layers are formed by filling a culture fluid 40 to a flow passage between a flow passage plate 211 and the semipermeable membrane 210 to culture cells 30 on one surface of the semipermeable membrane 210 and by filling a culture fluid 41 to a flow passage between a flow passage plate 213 and the semipermeable membrane 210 to culture cells 31 on the other surface of the semipermeable membrane 210.

While the cells cultured in the embodiment have a size of, typically, 8 μm to 10 μm, the semipermeable membrane 210 in the conventional biological tissue forming device 20 has hole diameters of approximately 3 μm. Therefore, when the conventional biological tissue forming device 20 is used, the cells between the cell layers are prevented from contacting one another, thereby leading to a problem of the reduced interaction between the cell layers, and the holes of the semipermeable membrane 210 are blocked as the cells grow, thereby leading to a problem of the reduced exchange efficiency of the liquid components.

In contrast to this, the biological tissue forming device 1 of the embodiment can form the two cell layers by filling the culture fluid 40 to the flow passage 110 between the flow passage plate 11 and the culture membrane 10 to culture the cells 30 on one surface of the culture membrane 10 and by filling the culture fluid 41 to the flow passage 130 between the flow passage plate 13 and the culture membrane 10 to culture the cells 31 on the other surface of the culture membrane 10, as illustrated in FIG. 4.

After the two cell layers are formed, the readily-soluble material 101 in the culture membrane 10 is dissolved to allow the cells to contact one another between the cell layers, thereby ensuring a solution to the problem of the reduced interaction between the cell layers. The liquid components can also be exchanged with high efficiency, thereby ensuring a solution to the problem of the reduced exchange efficiency of the liquid components between the two cell layers.

At this time, when the readily-soluble material 101 is the alginic acid, the alginic acid degrading enzyme is supplied to at least any one of the flow passage 110 and the flow passage 130 in the step of dissolving the culture membrane 10, and thus, the culture membrane 10 can be dissolved.

When the readily-soluble material 101 is the polyvinyl alcohol, the biological tissue forming device 1 is heated in the step of dissolving the culture membrane 10, and thus, the culture membrane 10 can be dissolved.

The step of dissolving the culture membrane 10 is preferably performed at a time point where the cell layers are formed on the entire culture regions.

It is preferred to form the cell layers formed of the adherent cells of respective different kinds in the flow passage 110 and the flow passage 130.

When the method for forming a biological tissue of the embodiment is such a method, it is possible to preferably form a biological tissue having the cell layers formed of a plurality of the different cells.

Here, it is necessary to attach the adherent cells on both the surfaces of the culture membrane 10 for culturing the adherent cells in the two flow passages in the biological tissue forming device 1.

For such a method, the adherent cells can be attached on both the surfaces of the culture membrane 10 by culturing the cells while vertically inverting the biological tissue forming device 1 after supplying the adherent cells and the culture fluid in the two flow passages in the biological tissue forming device 1.

It is also possible, without vertically inverting the biological tissue forming device 1, to attach the adherent cells also on a lower surface of the culture membrane 10 as well as on an upper surface of the culture membrane 10 by filling the adherent cells in the flow passage 130 at a lower side in the biological tissue forming device 1 when the adherent cells and the culture fluid are supplied to the two flow passages in the biological tissue forming device 1.

In this case, it is possible to keep the adherent cells on the lower surface of the culture membrane 10 in the attached state by washing away the cells remaining in the flow passage 130 with the culture fluid or the like after attaching the adherent cells on the lower surface of the culture membrane 10.

While this method wastes the cells, this method has an advantage that the adherent cells can be attached in a short time compared with the former method.

In the method for forming a biological tissue of the embodiment, for the adherent cells, for example, pluripotent stem cells (for example iPS cells) and embryonic stem cells (ES cells) are preferably usable.

The kind of the manufactured biological tissue is not specifically limited, and various biological tissues, such as a biological tissue in a proximal convoluted tubule model including a tissue formed of renal tubular epithelial cells and a tissue formed of vascular endothelial cells and biological tissues in a glomerulus model, a small bowel model, a liver model, and a lung model, can be a target.

Furthermore, the used culture fluid, its flow speed in the flow passage, and the like are also not specifically limited, and they can be appropriately set according to the cultured cells and tissues.

As described above, with the biological tissue forming device and the method for forming a biological tissue of the embodiment, the culture membrane can be configured using the readily-soluble material in, for example, an organ-on-a-chip, and dissolving the readily-soluble material after forming the cell layers on both the surfaces of this culture membrane ensures the cell-cell interaction and the exchange of liquid components between the cell layers of the formed biological tissue with high efficiency.

Second Embodiment

Next, a biological tissue forming device according to the second embodiment of the present invention will be described.

The biological tissue forming device of the embodiment is different from the first embodiment in that the culture membrane is formed of the readily-soluble material and the poorly-soluble material. Other configurations are similar to those of the first embodiment except for those described below.

That is, the biological tissue forming device of the embodiment has both surfaces on which culture regions of the adherent cells are disposed, and includes a culture membrane arranged between the plurality of cell layers after the adherent cells are cultured and a plurality of flow passages divided by the culture membrane. The culture membrane is formed of the readily-soluble material and the poorly-soluble material.

The biological tissue forming device of the embodiment will be described with reference numerals of the configuration similar to the first embodiment in FIGS. 1 to 3 to which a is attached.

In a biological tissue forming device 1a of the embodiment, a culture membrane 10a is formed of a readily-soluble material 101a and a poorly-soluble material 102a.

After the cell layers are formed, the readily-soluble material 101a in the culture membrane 10a is dissolved, and thus, only the poorly-soluble material 102a in the culture membrane 10a remains as a support body for the cell layers. This forms holes that pass through the culture membrane 10a.

That is, in a culture step of the adherent cells, the readily-soluble material 101a and the poorly-soluble material 102a in the culture membrane 10a are a scaffold for the adherent cells. After the dissolution of the readily-soluble material 101a, the poorly-soluble material 102a is the support body for the cell layers.

For the readily-soluble material 101a, for example, a water-soluble polymer is usable, and, for example, polyvinyl alcohol (PVA), alginic acid, and methyl cellulose are preferably usable.

When the alginic acid is used as the readily-soluble material 101a, feeding an alginic acid degrading enzyme into a flow passage 110a or a flow passage 130a ensures dissolving the readily-soluble material 101a in the culture membrane 10a in the biological tissue forming device 1.

When the polyvinyl alcohol is used as the readily-soluble material 101a, heating the biological tissue forming device 1a to, for example, 37° C. to 50° C. after forming the cell layers ensures dissolving the readily-soluble material 101a in the culture membrane 10a in the biological tissue forming device 1a.

Furthermore, when the methyl cellulose is used as the readily-soluble material 101a, cooling the biological tissue forming device 1a to, for example, 5° C. to 10° C. after forming the cell layers ensures dissolving the readily-soluble material 101a in the culture membrane 10a in the biological tissue forming device 1a.

For the poorly-soluble material 102a, for example, polyethylene terephthalate (PET), polylactic acid (PLA), and an ultraviolet ray (UV) curable resin are usable.

A porous membrane formed of the poorly-soluble material has hole diameters preferred to be a diameter of 10 microns or more. Thus setting the hole diameters ensures the cell-cell interaction and the exchange of liquid components between the two cell layers with high efficiency.

Thus, with the biological tissue forming device 1a of the embodiment, dissolving the readily-soluble material 101a in the culture membrane 10a after forming the cell layers ensures preferably performing the cell-cell interaction and the transmission of the liquid components between the plurality of cell layers.

The poorly-soluble material 102a in the culture membrane 10a can remain between the plurality of cell layers, thereby ensuring making the cell layers irrefrangible as the support body of the poorly-soluble material 102a.

The culture membrane 10a in the biological tissue forming device 1a of the embodiment can be manufactured in, for example, the following method and be used.

Figure 5:
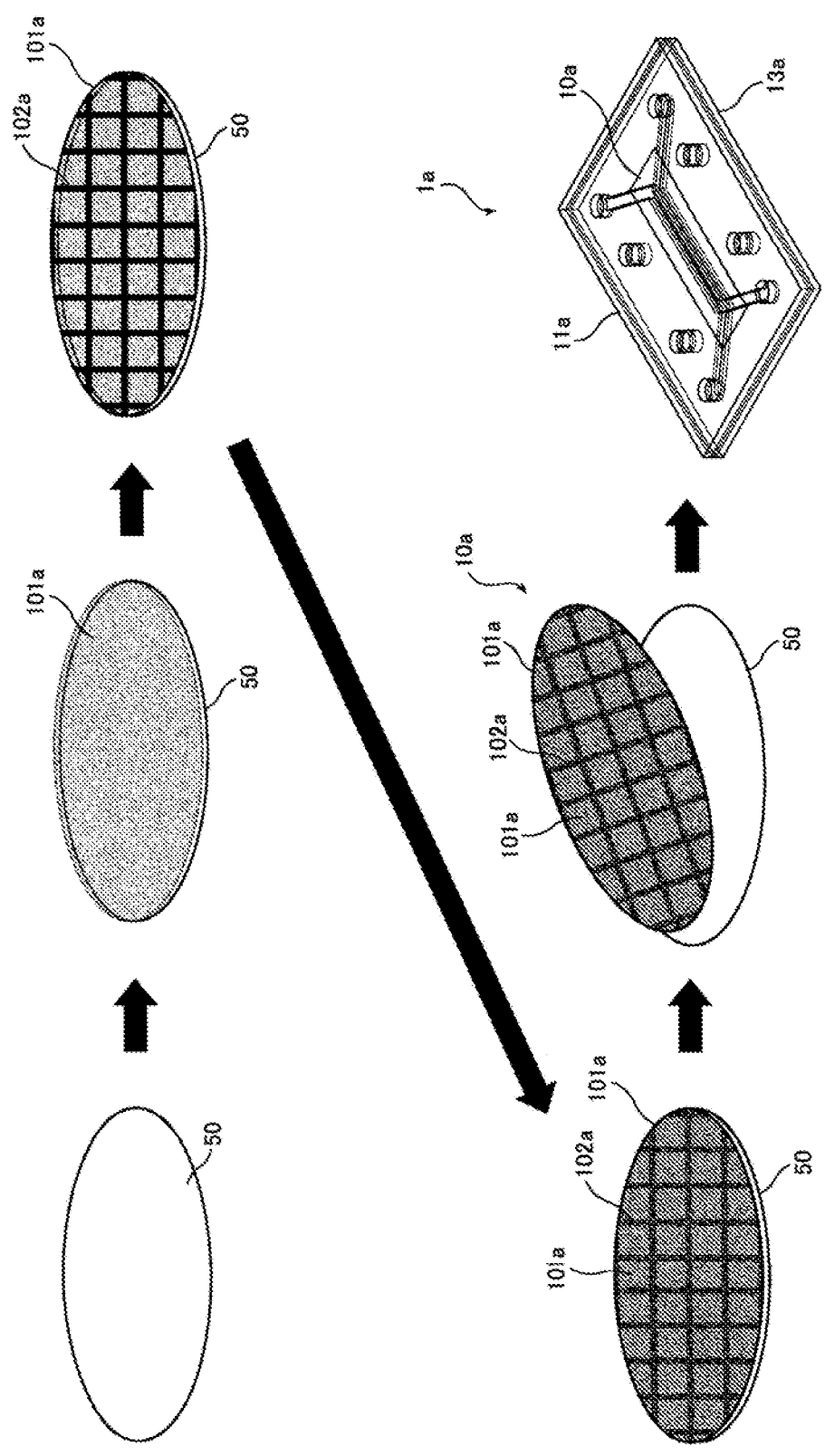
FIG. 5 is a schematic diagram illustrating a manufacturing process of a culture membrane in a biological tissue forming device according to a second embodiment of the present invention.

That is, as illustrated in FIG. 5, first, the readily-soluble material 101a is applied over a base material 50. Next, the poorly-soluble material 102a is laminated and the readily-soluble material 101a is additionally applied. The obtained culture membrane 10a is then stripped off of the base material 50 and cut into a desired shape, and is arranged in the biological tissue forming device 1.

For the readily-soluble material 101a in the culture membrane 10a in the biological tissue forming device 1a of the embodiment, the alginic acid, the polyvinyl alcohol, and the like are usable as described above. For the poorly-soluble material 102a in the same culture membrane 10a, the polyethylene terephthalate (PET), the polylactic acid (PLA), the ultraviolet ray (UV) curable resin, and the like are usable. Furthermore, the obtained culture membrane 10a can be cut into the desired shape and used as described above.

Flow passage plates 11a, 13a and the culture membrane 10a are attached together with adhesive layers 12a, 14a to ensure manufacturing the biological tissue forming device 1a of the embodiment.

The biological tissue forming device 1a of the embodiment may be in a state before the cell layers are formed on the culture membrane 10a or may be in a state after the cell layers are formed on the culture membrane 10a.

The biological tissue forming device 1a of the embodiment includes one that has the readily-soluble material 101a dissolved, the poorly-soluble material 102a remaining, and the holes passing through the culture membrane 10a formed after the cell layers are formed on the culture membrane 10a.

Furthermore, it is also preferred that the biological tissue forming device 1a of the embodiment is formed with the culture membrane 10a including the adherent cells. In such a case, the configuration may have the adherent cells fixed on the surfaces of the culture membrane 10a or the configuration may have the adherent cells contained in the readily-soluble material 101a in the culture membrane 10a.

The method for forming a biological tissue of the embodiment is a method for forming a biological tissue having a plurality of cell layers formed of adherent cells and includes a step of supplying the adherent cells and a culture fluid to two flow passages in a biological tissue forming device having both surfaces on which culture regions of the adherent cells are disposed, including a culture membrane arranged between the plurality of cell layers after the adherent cells are cultured and the two flow passages divided by the culture membrane, the culture membrane being formed of a readily-soluble material and a poorly-soluble material, a step of culturing the adherent cells in the two flow passages to form the cell layers on both the surfaces of the culture membrane, and a step of dissolving the culture membrane.

Figure 6:
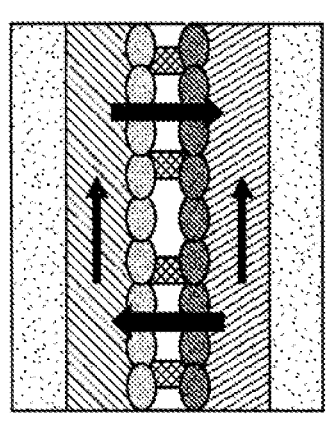
FIG. 6 is a schematic diagram illustrating a formation process of cell layers by the biological tissue forming device according to the second embodiment of the present invention.
Figure 6:
Figure 6:
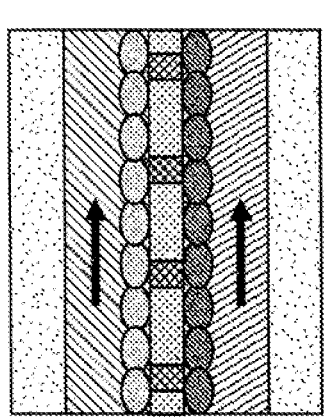
Figure 6:
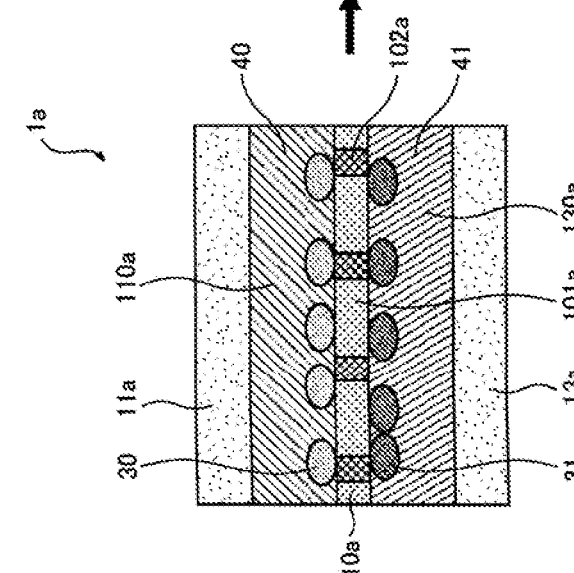

The biological tissue forming device 1a of the embodiment can form the two cell layers by filling the culture fluid 40 to the flow passage 110a between the flow passage plate 11a and the culture membrane 10a to culture the cells 30 on one surface of the culture membrane 10a and by filling the culture fluid 41 to the flow passage 130a between the flow passage plate 13a and the culture membrane 10a to culture the cells 31 on the other surface of the culture membrane 10a, as illustrated in FIG. 6.

After the two cell layers are formed, the readily-soluble material 101a in the culture membrane 10a is dissolved to allow the cells to contact one another between the cell layers, thereby ensuring a solution to the problem of the reduced interaction between the cell layers. The liquid components can be exchanged with high efficiency, thereby ensuring a solution to the problem of the reduced exchange efficiency of the liquid components between the two cell layers.

Since the poorly-soluble material 102a in the culture membrane 10a does not dissolve, this can remain between the two cell layers, thereby ensuring making the cell layers irrefrangible as the support body of the poorly-soluble material 102a.

At this time, when the readily-soluble material 101a is the alginic acid, the alginic acid degrading enzyme is supplied to at least any one of the flow passage 110a and the flow passage 130a in the step of dissolving the readily-soluble material of the culture membrane 10a, and thus, the culture membrane 10a can be dissolved.

When the readily-soluble material 101a is the polyvinyl alcohol, the biological tissue forming device 1a is heated in the step of dissolving the readily-soluble material in the culture membrane 10a, and thus, the culture membrane 10a can be dissolved.

As described above, with the biological tissue forming device and the method for forming a biological tissue of the embodiment, the culture membrane can be configured using the readily-soluble material and the poorly-soluble material in, for example, an organ-on-a-chip, and dissolving the readily-soluble material after forming the cell layers on both the surfaces of this culture membrane ensures the cell-cell interaction and the exchange of liquid components between the cell layers of the formed biological tissue with high efficiency, and ensures making the cell layers irrefrangible.

EXAMPLES

The following describes experiments that were performed for confirming the dissolution of the readily-soluble material used in the biological tissue forming device according to the embodiment of the present invention. The readily-soluble material is used as the culture membrane arranged between the plurality of cell layers after the adherent cells are cultured in the biological tissue forming device, and is dissolved after the cell layers are formed, but the formations of the cell layers were omitted in the respective examples and only solubility of the readily-soluble materials was evaluated.

The culture fluid is used when the cell layers are formed using the biological tissue forming device, but in the respective examples and the reference examples, a phosphate buffer solution was used instead of the culture fluid and the solubility was evaluated. Those results are shown in Table 1 below (results of experiments carried out for confirming dissolutions of readily-soluble materials used in the biological tissue forming device according to the first embodiment of the present invention).

culture period for forming the cell layers and it is desired that the dissolution does not take place during the period. The reason for confirming the transparency of the readily-soluble material is that since the cell layers are formed on the surface of the readily-soluble material, it is desired that the readily-soluble material is transparent in observing the cell layers as it is easy to be visually perceived.

As the result of the above-described confirmation, the surface of the readily-soluble material was slightly dissolved by sodium chloride contained in the phosphate buffer solution, and therefore, the transparency was deteriorated.

TABLE 1

|  | EXAMPLE 1 | EXAMPLE 2 | EXAMPLE 3 |
|---|---|---|---|
| MATERIAL | CALCIUM ALGINATE | CALCIUM ALGINATE | POLYVINYL ALCOHOL |
| FILM THICKNESS | 10 μm | 10 μm | 7 μm |
| TRANSPARENCY AFTER IMMERSION | NONTRANSPARENT | NONTRANSPARENT | TRANSPARENT |
| DISSOLVING METHOD | SODIUM CITRATE | ALGINIC ACID DEGRADING ENZYME | TEMPERATURE |
| DISSOLUTION CONDITION | 37° C.-6 HOURS | 37° C.-6 HOURS | 50° C.-3 HOURS |
| SOLUBILITY | EXCELLENT (DISSOLVED) | EXCELLENT (DISSOLVED) | EXCELLENT (DISSOLVED) |

|  | EXAMPLE 4 | EXAMPLE 5 | REFERENCE EXAMPLE 1 |
|---|---|---|---|
| MATERIAL | METHYL CELLULOSE | METHYL CELLULOSE (+STYRENESULFONIC ACID SODIUM) | PET MEMBRANE |
| FILM THICKNESS | 20 μm | 20 μm | 9 μm |
| TRANSPARENCY AFTER IMMERSION | TRANSPARENT | TRANSPARENT | TRANSPARENT |
| DISSOLVING METHOD | TEMPERATURE | TEMPERATURE | — |
| DISSOLUTION CONDITION | 10° C.-10 MINUTES | 10° C.-10 MINUTES | — |
| SOLUBILITY | GOOD (DISSOLVED) | EXCELLENT (DISSOLVED) | POOR (NOT DISSOLVED) |

Example 1

In this Example, an experiment that used alginic acid as the readily-soluble material in the biological tissue forming device, and dissolved this with sodium citrate was performed.

Specifically, sodium alginate (FUJIFILM Wako Pure Chemical Corporation, 194-13321) was dissolved in a pure water to prepare a 1% sodium alginate aqueous solution. This sodium alginate aqueous solution was casted on a PET film and was dried for one night at room temperature (25° C.).

Next, the resultant product was immersed in a 0.5 M calcium chloride aqueous solution for ten minutes to cross-link the alginic acid, and thereafter, was rinsed with a pure water. The resultant product was dried for one night at room temperature (25° C.), and thus, a calcium alginate thin film (film thickness of approximately 10 μm) was manufactured to be the readily-soluble material. The readily-soluble material cut out into a 10 mm square was immersed in a 20 mL of a phosphate buffer solution (Thermo Fisher Scientific Inc., 10010023) and stored for one week at a temperature of 37° C., and thereafter, the state and the transparency of the readily-soluble material were confirmed.

Here, the reason for storing the readily-soluble material for one week before it was dissolved and confirming the state is because it typically needs approximately one week of In order to dissolve the readily-soluble material, the sodium citrate was added into the phosphate buffer solution so as to be 1%, and was immersed in the phosphate buffer solution for six hours at a temperature of 37° C. As the result, the readily-soluble material was completely dissolved in the phosphate buffer solution.

Example 2

In this example, an experiment that used alginic acid as the readily-soluble material in the biological tissue forming device, and dissolved this with an alginic acid degrading enzyme was performed.

Specifically, similarly to Example 1, a calcium alginate thin film was manufactured to be used as the readily-soluble material, was immersed in a phosphate buffer solution and stored, and thereafter, the state and the transparency of the readily-soluble material were confirmed. As the result, the state and the transparency of the readily-soluble material compared favorably with that before being immersed in the phosphate buffer solution.

In order to dissolve this readily-soluble material, 100 μg of an alginic acid degrading enzyme (NIPPON GENE CO., LTD., 319-08261) was added to the phosphate buffer solution, and was immersed in the phosphate buffer solution for six hours at a temperature of 37° C. As the result, the readily-soluble material was completely dissolved in the phosphate buffer solution.

Example 3

In this example, an experiment that used polyvinyl alcohol as the readily-soluble material in the biological tissue forming device, and dissolved this by heating was performed.

Specifically, polyvinyl alcohol (FUJIFILM Wako Pure Chemical Corporation, 160-11485) was dissolved in a pure water to prepare a 5% polyvinyl alcohol aqueous solution. This polyvinyl alcohol aqueous solution was casted on a PET film and was dried for one night at room temperature (25° C.), and thus, a polyvinyl alcohol thin film (film thickness of approximately 7 μm) was manufactured to be the readily-soluble material.

Next, the readily-soluble material cut out into a 10 mm square was immersed in a 20 mL of a phosphate buffer solution (Thermo Fisher Scientific Inc., 10010023) and stored for one week at a temperature of 37° C., and thereafter, the state and the transparency of the readily-soluble material were confirmed. As the result, the state and the transparency of the readily-soluble material compared favorably with that before being immersed in the phosphate buffer solution.

In order to dissolve this readily-soluble material, it was immersed for three hours at a temperature of 50° C. in the phosphate buffer solution. As the result, the readily-soluble material was completely dissolved in the phosphate buffer solution.

Example 4

In this example, an experiment that used methyl cellulose as the readily-soluble material in the biological tissue forming device, and dissolved this by cooling was performed.

Specifically, methyl cellulose (manufactured by Shin-Etsu Chemical Co., Ltd., MCE-4000) was dissolved in a pure water to prepare a 1% methyl cellulose aqueous solution. This methyl cellulose aqueous solution was casted on a PET film and was dried for one night at room temperature (25° C.), and thus, a methyl cellulose thin film (film thickness of approximately 20 μm) was manufactured to be the readily-soluble material.

Next, the readily-soluble material cut out into a 10 mm square was immersed in a 20 mL of a phosphate buffer solution (Thermo Fisher Scientific Inc., 10010023) and stored for one week at a temperature of 37° C., and thereafter, the state and the transparency of the readily-soluble material were confirmed. As the result, the state and the transparency of the readily-soluble material compared favorably with that before being immersed in the phosphate buffer solution.

In order to dissolve this readily-soluble material, it was immersed in the phosphate buffer solution for ten minutes at a temperature of 10° C. As the result, the readily-soluble material was partly dissolved in the phosphate buffer solution.

Note that when the readily-soluble material was stored at a temperature of 5° C. in order to be dissolved, the readily-soluble material dissolved more in the phosphate buffer solution. Therefore, in order to make it possible to dissolve better the readily-soluble material in the phosphate buffer solution at a temperature of 10° C., an experiment in which the dissolution temperature of the methyl cellulose aqueous solution was adjusted was performed as follows.

Example 5

In this example, an experiment that used methyl cellulose as the readily-soluble material in the biological tissue forming device, added styrenesulfonic acid sodium as an additive, and dissolved them by cooling was performed.

Specifically, styrenesulfonic acid sodium (FUJIFILM Wako Pure Chemical Corporation, 192-03292) was added to a methyl cellulose aqueous solution prepared similarly to Example 4 to be 0.1 M in order to adjust the dissolution temperature. This methyl cellulose aqueous solution was casted on a PET film and was dried for one night at room temperature (25° C.), and thus, a methyl cellulose thin film (film thickness of approximately 20 μm) was manufactured to be the readily-soluble material.

Next, the readily-soluble material cut out into a 10 mm square was immersed in a 20 mL of a phosphate buffer solution (Thermo Fisher Scientific Inc., 10010023) and stored for one week at a temperature of 37° C., and thereafter, the state and the transparency of the readily-soluble material were confirmed. As the result, the state and the transparency of the readily-soluble material compared favorably with that before being immersed in the phosphate buffer solution.

In order to dissolve this readily-soluble material, it was immersed in the phosphate buffer solution for ten minutes at a temperature of 10° C. As the result, the readily-soluble material was completely dissolved in the phosphate buffer solution.

Reference Example 1

In the reference example, an experiment that changed the readily-soluble material in the biological tissue forming device to a PET membrane (Corning Inc., 353091) as a commercially available semipermeable membrane and dissolved this was performed.

Specifically, the PET membrane cut out into a 10 mm square was immersed in a 20 mL of a phosphate buffer solution (Thermo Fisher Scientific Inc., 10010023) and stored for one week at a temperature of 37° C., and thereafter, the state and the transparency of the readily-soluble material were confirmed. As the result, the state and the transparency of the readily-soluble material compared favorably with that before being immersed in the phosphate buffer solution.

This PET membrane was also immersed in the phosphate buffer solution for 24 hours at a temperature of 90° C. As the result, the PET membrane did not dissolve and no change was observed.

Furthermore, Savinase (Novozymes A/S, 16L) was added to be 0.5% in order to decompose this PET membrane with an enzyme, and was stored for 24 hours at a temperature of 37° C. As the result, the PET membrane did not dissolve and no change was observed.

From the result of Reference Example 1, it was found that the PET membrane was not usable as an alternative of the readily-soluble material in the biological tissue forming device. On the other hand, it was found that the PET membrane was preferably usable as the poorly-soluble material in the biological tissue forming device.

The present invention is not limited to the above-mentioned embodiments and examples, and it is needless to say that various modifications are possible within the scope of the present invention.

For example, the shape of the flow passage and the shape of the culture membrane in the biological tissue forming device are not limited to those illustrated in FIG. 1 and the like, and can be appropriately changed to any other shapes.

INDUSTRIAL APPLICABILITY

The present invention can be preferably used, for example, for a case where a biological tissue is formed using, for example, an organ-on-a-chip.

The documents described in the specification and the Japanese patent application claiming the priority under the Paris Convention to the invention are incorporated herein by reference in its entirety.

DESCRIPTION OF REFERENCE SIGNS 1, 1a: Biological tissue forming device
10, 10a: Culture membrane
101, 101a: Readily-soluble material
102a: Poorly-soluble material
11, 11a, 13, 13a: Flow passage plate
110, 110a, 130, 130a: Flow passage
12, 12a, 14, 14a: Adhesive layer
20: Biological tissue forming device
210: Semipermeable membrane
211, 213: Flow passage plate
30, 31: Cell
40, 41: Culture fluid
50: Base material

The invention claimed is:

1. A method for forming a biological tissue having a plurality of cell layers formed of adherent cells, the method comprising:

a step of supplying the adherent cells and a culture fluid to two flow passages in a biological tissue forming device, the biological tissue forming device having both surfaces on which culture regions of the adherent cells are disposed, the biological tissue forming device including a culture membrane arranged between the plurality of cell layers after the adherent cells are cultured and the two flow passages divided by the culture membrane, the culture membrane being formed of a readily-soluble material and a poorly-soluble material;

a step of culturing the adherent cells in the two flow passages to form the cell layers on both the surfaces of the culture membrane; and a step of dissolving the readily-soluble material in the culture membrane, wherein the readily-soluble material in the culture membrane is dissolved to form holes that pass through the culture membrane.

2. The method for forming a biological tissue according to claim 1, wherein the readily-soluble material is alginic acid, an alginic acid degrading enzyme is supplied to at least any one of the two flow passages in the step of dissolving, and the readily-soluble material in the culture membrane is dissolved.

3. The method for forming a biological tissue according to claim 1, wherein the readily-soluble material is polyvinyl alcohol, the biological tissue forming device is heated in the step of dissolving, and the readily-soluble material in the culture membrane is dissolved.

4. The method for forming a biological tissue according to claim 1, wherein the readily-soluble material is methyl cellulose, the biological tissue forming device is cooled in the step of dissolving, and the readily-soluble material in the culture membrane is dissolved.

5. The method for forming a biological tissue according to claim 1, wherein the step of dissolving the culture membrane is performed at a time point where the cell layer is formed in the entire culture regions.

6. The method for forming a biological tissue according to claim 1, wherein in the two flow passages, cell layers formed of adherent cells of respective different kinds are formed.

* * * * *